US009492188B2

(12) United States Patent
Abri et al.

(10) Patent No.: US 9,492,188 B2
(45) Date of Patent: Nov. 15, 2016

(54) ENDOSCOPIC INSTRUMENT

(71) Applicant: Karl Storz GmbH & Co. KG, Tuttlingen (DE)

(72) Inventors: Omid Abri, Berlin (DE); Stephan Schrader, Kleinmachnow (DE); Jonas Forster, Berlin (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 166 days.

(21) Appl. No.: 14/309,592

(22) Filed: Jun. 19, 2014

(65) Prior Publication Data

US 2014/0379014 A1 Dec. 25, 2014

(30) Foreign Application Priority Data

Jun. 20, 2013 (DE) .................. 10 2013 106 446

(51) Int. Cl.
| | |
|---|---|
| *A61B 17/28* | (2006.01) |
| *A61B 17/32* | (2006.01) |
| *A61B 17/3201* | (2006.01) |
| *A61B 17/29* | (2006.01) |

(52) U.S. Cl.
CPC .......... *A61B 17/2804* (2013.01); *A61B 17/29* (2013.01); *A61B 17/3201* (2013.01); *A61B 17/320016* (2013.01); *A61B 34/30* (2016.02); *A61B 2017/2927* (2013.01); *A61B 2017/2938* (2013.01); *A61B 2017/2939* (2013.01); *A61B 2017/2947* (2013.01); *A61B 2034/305* (2016.02)

(58) Field of Classification Search
CPC ................ A61B 17/2804; A61B 17/320016; A61B 17/3201; A61B 17/29; A61B 19/2203; A61B 2017/2938; A61B 2017/2939; A61B 2017/2927; A61B 2017/2947; A61B 2019/2234

See application file for complete search history.

(56) References Cited

U.S. PATENT DOCUMENTS

| | | | |
|---|---|---|---|
| 6,582,451 B1 * | 6/2003 | Marucci | A61B 17/29 |
| | | | 606/207 |
| 6,699,235 B2 | 3/2004 | Wallace et al. | |
| 7,121,781 B2 | 10/2006 | Sanchez | |
| 2002/0143358 A1 | 10/2002 | Domingo et al. | |
| 2002/0156497 A1 | 10/2002 | Nagase et al. | |
| 2004/0253079 A1 | 12/2004 | Sanchez | |
| 2006/0229666 A1 | 10/2006 | Suzuki et al. | |
| 2008/0058861 A1 | 3/2008 | Cooper et al. | |
| 2012/0296356 A1 | 11/2012 | Balanev et al. | |

* cited by examiner

*Primary Examiner* — Julian W Woo
(74) *Attorney, Agent, or Firm* — Whitmyer IP Group LLC (57) ABSTRACT

Endoscopic instrument having a proximal end, a distal end, a longitudinal direction along which the endoscopic instrument extends from the proximal end to the distal end, an end effector on the distal end, which end effector has a first end effector part and a second end effector part, a connecting element on the distal end, on which connecting element the first and second end effector parts are mounted and which connecting element extends along a transverse direction, a first pushing element, a second pushing element, a third pushing element, and a fourth pushing element, wherein the pushing elements each extend along the longitudinal direction and are displaceable relative to one another along the longitudinal direction, and wherein the first pushing element is articulately arranged at the first end effector part, the second pushing element is articulately arranged at the second end effector part, the third pushing element is articulately arranged at the connecting element, and the fourth pushing element is articulately arranged at the connecting element.

21 Claims, 8 Drawing Sheets

ENDOSCOPIC INSTRUMENT

CROSS REFERENCES TO RELATED APPLICATIONS

This application claims priority from German patent application 10 2013 106 446.9, filed on Jun. 20, 2013. The entire contents of this priority application is incorporated herein by reference.

BACKGROUND

The present disclosure relates to an endoscopic instrument.

Conventional instruments for minimally invasive surgery (MIS) are rigid from the handle (proximal end) to the end effector (distal end), which is in particular a gripper or scissors. Here, there are normally two degrees of freedom available to the surgeon. Firstly, the shaft, and thus the end effector, can be rotated. Secondly, the end effector can be opened and closed.

Although it is possible for the surgeon to displace the endoscopic instrument laterally, this constitutes only a limited freedom of movement. Said freedom of movement becomes ever smaller the greater the depth to which a surgeon must insert the endoscopic instrument into the body of a patient, and the more sensitive the surrounding tissue is that could be damaged by a lateral displacement of the instrument.

Similar problems are also encountered by technicians who have to work with an endoscopic instrument in constricted technical spaces, for example in an engine. Both the surgeon and also the technician are restricted by the limited maneuverability and must attempt to compensate for these limitations through increased dexterity and experience.

In the prior art, various solutions have therefore been proposed for improving the mobility of the endoscopic instrument at its distal end.

U.S. Pat. No. 6,699,235 presents an endoscopic instrument which, at the distal end, can be pivoted in two mutually perpendicular planes. The apparatus is however primarily used with an end effector that does not require its own degree of freedom for its actuation, such as for example an end effector for cauterising.

US 2008/0058861 presents an endoscopic instrument having a movable distal end on which a gripper is arranged. The construction of said instrument is however highly complex and does not provide the surgeon with direct haptic feedback as he is working.

U.S. Pat. No. 7,121,781 presents an endoscopic instrument whose distal end is mounted pivotably on a ball joint. Three pins make it possible for the distal gripper end to be displaced about two axes and for the end effector to be opened and closed. The actuation of the end effector must be performed under the control of a machine. Furthermore, there is no direct haptic feedback to the surgeon.

SUMMARY

It is an object to provide an improved endoscopic instrument which provides the surgeon with adequate freedom for the actuation of the end effector while the endoscopic instrument is in use. Here, the surgical instrument should in particular be of mechanically simple construction and permit direct haptic feedback to the surgeon. Here, the endoscopic instrument should also be as intuitive as possible to operate, such that the movements of the surgeon's hand are transmitted directly to the end effector.

According to one aspect, there is provided an endoscopic instrument having:
 a proximal end,
 a distal end,
 a longitudinal direction along which the endoscopic instrument extends from the proximal end to the distal end,
 an end effector on the distal end, which end effector has a first end effector part and a second end effector part,
 a connecting element on the distal end, on which connecting element the first and second end effector parts are mounted and which connecting element extends along a transverse direction,
 a first pushing element,
 a second pushing element,
 a third pushing element, and
 a fourth pushing element,
 wherein the pushing elements each extend along the longitudinal direction and are displaceable relative to one another along the longitudinal direction, and
 wherein the first pushing element is articulately arranged at the first end effector part, the second pushing element is articulately arranged at the second end effector part, the third pushing element is articulately arranged at the connecting element, and the fourth pushing element is articulately arranged at the connecting element.

One special feature of this endoscopic instrument can be seen in the fact that numerous degrees of freedom can be realized by the fourth pushing elements, which extend, according to some exemplary embodiments, into the proximal end of the endoscopic instrument. It is accordingly possible for the first and second end effector parts, which constitute an end effector or at least one assembly of the end effector, to be displaced relative to one another, specifically in relation to the connecting element on which the first and second end effector parts are mounted.

It is furthermore possible for the two end effector parts to be displaced concordantly and uniformly, such that the end effector can be pivoted in a first plane which is perpendicular to the transverse direction along which the connecting element extends. It is furthermore possible for the end effector to be pivoted in a second plane which is perpendicular to the first plane and which is spanned by the longitudinal direction and the transverse direction.

A simultaneous displacement of the first and of the second end effector part in the first plane and in the second plane is also possible. In this way, the end effector can be pivoted in all directions; according to some exemplary embodiments, oval or circular movements of the end effector are also possible. The endoscopic instrument can furthermore be displaced along its longitudinal direction and rotated about a longitudinal axis along the longitudinal direction.

It is pointed out at this juncture that the expressions "longitudinal direction", "longitudinal axis" "transverse direction", "transverse axis", "vertical direction" and "vertical axis" which have been introduced above and which will appear again below serve merely for improved reader guidance and for ease of understanding of the structural design. The use of these expressions does not serve to establish a particular relationship with respect to some other reference system, such as for example the gravitational field of the Earth.

The various expressions are rather intended to highlight that certain extents of the endoscopic instrument can be oriented, and movements of the end effector can take place, in different directions. Here, the longitudinal direction and transverse direction, longitudinal direction and vertical direction, and transverse direction and vertical direction are in each case at an angle relative to one another, that is to say point in different spatial directions. Here, the endoscopic instrument can be oriented such that the longitudinal direction, transverse direction and vertical direction, in each case in pairs, are at an angle of at least 45°, according to other exemplary embodiments of at least 75° and according to yet other exemplary embodiments of at least 85° with respect to one another, and according to still other exemplary embodiments are at least substantially perpendicular to one another.

According to some exemplary embodiments, the vertical direction is to be understood as being perpendicular to the transverse direction. Since the first and second end effector parts are pivotable relative to one another, a first vertical axis of the first end effector part and a second vertical axis of the second end effector part do not have to coincide or be parallel in all positions of the end effector. Rather, during the actuation of the end effector part, in particular during an opening and closing process, an angle will be generated between the first and second vertical axes. The first and second vertical axes however remain, aside from in extreme positions of the end effector part, in each case at an angle both with respect to the transverse direction and also with respect to the longitudinal direction, and, in terms of their orientation, can thus be technically distinguished from the longitudinal direction and the transverse direction.

The reader guidance aid that is intended to be provided by these designations will be explained once again in the figures.

The pushing elements extend in each case along the longitudinal direction, that is to say along the direction in which the endoscopic instrument extends from the proximal end to the distal end.

It is pointed out that the designations "pushing element", "pushing rod" and "pushing force" are to be understood both in the sense of positive pushing and also in the sense of negative pushing, also referred to as pulling. The expressions are used merely as a linguistic simplification for improved understanding of the disclosure.

The coupling between the first pushing element, the first end effector part, the second pushing element and the second end effector part is configured according to some exemplary embodiments such that a displacement of the first pushing element and of the second pushing element toward the distal end moves the first and second end effector parts toward one another in a closing direction, and such that a displacement of the first pushing element and of the second pushing element toward the proximal end moves the first and second end effector parts away from one another in an opening direction. In particular, said coupling is configured so as to be independent of a movement of the third and fourth pushing elements, such that the coupling takes place according to some exemplary embodiments without a displacement of the third and fourth pushing elements, and the third and fourth pushing elements are not imperatively displaced as a result of the displacement of the first and second pushing elements.

The coupling between the first pushing element, the first end effector part, the second pushing element and the second end effector part is configured according to some exemplary embodiments such that an opposing displacement of the first pushing element and second pushing element with respect to the longitudinal direction causes a pivoting of the first and second end effector parts about the connecting element. In particular, said coupling is configured so as to be independent of a movement of the third and fourth pushing elements, such that the coupling according to some exemplary embodiments takes place without a displacement of the third and fourth pushing elements and the third and fourth pushing elements are not imperatively displaced as a result of the displacement of the first and second pushing elements.

According to some exemplary embodiments the coupling between the third pushing element, the fourth pushing element and the connecting element is configured such that an opposing displacement of the third pushing element and of the fourth pushing element with respect to the longitudinal direction causes a conjoint pivoting movement of the first and second end effector parts in each case about a third and a fourth vertical axis, wherein the third vertical axis and the fourth vertical axis are in each case perpendicular to the transverse direction. If the third and fourth vertical axes coincide, this may define according to some exemplary embodiments the vertical direction along which the third and fourth vertical axes extend.

In one refinement, the first pushing element is articulately arranged at the first end effector part by a first joint, and/or the second pushing element is articulately arranged at the second end effector part by a second joint.

This refinement permits a good transmission of the pushing or tensile force from the pushing elements to the end effector parts. Furthermore, the end effector parts can be displaced in a precise manner. According to some exemplary embodiments, the two articulated mountings are each in the form of a joint. Alternatively, instead of a joint, use may also be made of an elastic component, composed for example of rubber or plastic.

In one refinement, the articulated mounting of the first pushing element is configured such that the first end effector part is displaceable relative to the first pushing element parallel to a pivot plane and can be pivoted about a transverse axis of the connecting element, wherein the pivot plane is an imaginary plane spanned by the longitudinal direction and the transverse direction.

Said form of articulated mounting permits a large number of degrees of freedom for the pivoting and actuation of the end effector.

According to some exemplary embodiments, alternatively or in addition, the articulated mounting of the second pushing element is configured such that the second end effector part is displaceable relative to the second pushing element parallel to a pivot plane and can be pivoted about a transverse axis of the connecting element, wherein the pivot plane is in turn an imaginary plane spanned by the longitudinal direction and the transverse direction.

In a further refinement, the articulated mounting of the third pushing element is configured such that the third pushing element and the connecting element are pivotable relative to one another about a pivot axis.

Said refinement permits good pivoting capability of the end effector. According to some embodiments the articulated mounting is configured such that a pivoting movement is possible only about the third vertical axis. As already explained, the third vertical axis may run along the vertical direction. In different operating states of the end effector part, the third vertical axis will however typically be at an angle with respect to the vertical direction.

Alternatively or in addition, according to some exemplary embodiments the articulated mounting of the fourth pushing element is configured such that the fourth pushing element and the connecting element are pivotable relative to one another about the pivot axis.

In one refinement, the articulated mounting of the third pushing element is configured such that a projection on the third pushing element engages into a recess of the connecting element or such that a projection on the connecting element engages into a recess of the third pushing element, or a third pin is inserted into two recesses of the connecting element and, between these, is guided through a recess on the third pushing element.

Said refinement offers a structurally simple facility for the articulated mounting. According to some exemplary embodiments, two projections on the third pushing element engage, along a third vertical axis, into recesses of the connecting element, or two projections on the connecting element engage into one or more recesses of the third pushing element.

According to some exemplary embodiments, alternatively or in addition, the articulated mounting of the fourth pushing element is configured such that a projection on the fourth pushing element engages into a recess of the connecting element or a projection on the connecting element engages into a recess of the fourth pushing element, or a fourth pin is inserted into two recesses of the connecting element and, between these, is guided through a recess on the fourth pushing element.

In one refinement, an imaginary elongation of a first vertical axis about which the first end effector part is pivotable relative to the first pushing element runs, with respect to the transverse direction, between articulation points of the third and fourth pushing element on the connecting element, according to some exemplary embodiments in the center between the articulation points.

Said refinement permits good controllability of the end effector. According to some exemplary embodiments, the imaginary elongation of the first vertical axis runs outside the center between the articulation points. According to some exemplary embodiments, the imaginary elongation of the first vertical axis runs through the articulation point of the third pushing element or the articulation point of the fourth pushing element.

In a further refinement, a first transverse axis about which the first end effector part is pivotable relative to the first pushing element is at least substantially parallel to the transverse direction.

Said refinement may be mechanically advantageous and may permit precise control of the end effector. With corresponding technical measures, it is however also possible for the first transverse axis to be configured so as to be at an angle with respect to the transverse direction.

According to some exemplary embodiments, alternatively or additionally, a second transverse axis about which the second end effector part is pivotable relative to the second pushing element is at least substantially parallel to the transverse direction.

In one refinement, the first joint has a first joint sleeve which is inserted rotatably into a recess on the first end effector part.

Said refinement makes it possible to realize a stable and effective guide which can be designed to be suitable for accommodating pushing forces. For this purpose, according to some exemplary embodiments, the joint sleeve lies areally against the recess. According to other exemplary embodiments, the joint sleeve is inserted into an at least substantially cylindrical recess. According to yet other exemplary embodiments, alternatively or in addition, the second joint has a second joint sleeve which is rotatably inserted into a second recess on the second end effector part.

In a refinement, the first pushing element is connected in positively locking fashion to the first joint sleeve.

Said refinement may be realized easily and is reliable. Here, available alternatives for the positively locking connection are, according to some exemplary embodiments, the same alternatives as those described above in conjunction with the articulated mounting of the third pushing element on the connecting element. Alternatively or in addition, the second pushing element is connected in positively locking fashion to the second joint sleeve.

In a further refinement, the first joint sleeve is rotatable only about a first vertical axis.

Said refinement permits precise control of the end effector because the joint sleeve provides precisely one degree of freedom, specifically a displacement about the first vertical axis. According to some exemplary embodiments, alternatively or in addition, the second joint sleeve is rotatable only about a second vertical axis, wherein the second vertical axis, including an imaginary elongation, coincides with the first vertical axis.

In a further refinement, the first pushing element is displaceable relative to the first joint sleeve only in an imaginary plane which is spanned by the longitudinal direction and the vertical direction.

This refinement also permits precise control of the end effector. As already stated, the vertical direction differs both from the longitudinal direction and also from the transverse direction and is, according to some exemplary embodiments, perpendicular to the transverse direction. According to some exemplary embodiments, alternatively or in addition, the second pushing element is displaceable relative to the second joint sleeve only in a second imaginary plane which is spanned by the longitudinal direction and a vertical direction.

In a further refinement, all of the pushing elements are arranged parallel to one another.

Said refinement is structurally simple and reliable. Furthermore, the diameter of the endoscopic instrument can thereby be kept small.

In a further refinement, the pushing elements are designed as pushing rods and/or, according to some exemplary embodiments, are designed to be entirely rectilinear.

Said refinement is also structurally simple and reliable.

In a further refinement, the first end effector part is in the form of a first gripping forceps part and the second end effector part is in the form of a second gripping forceps part, or the first end effector part is in the form of a first scissor part and the second end effector part is in the form of a second scissor part.

These refinements can make all of the required degrees of freedom available to the user in a simple manner. It is however basically also possible for other end effectors to be used, such as for example forceps, scissors, coagulation needles or fluid extractors, and jaw parts.

It is understood that the features mentioned above and the features yet to be explained below can be used not only in the respectively specified combination but also in other combinations or individually without departing from the scope of the present invention.

BRIEF DESCRIPTION OF THE DRAWINGS

Exemplary embodiments are illustrated in the drawing and will be explained in more detail in the following description. In the drawing.

DESCRIPTION OF EXEMPLARY EMBODIMENTS

Figure 1:
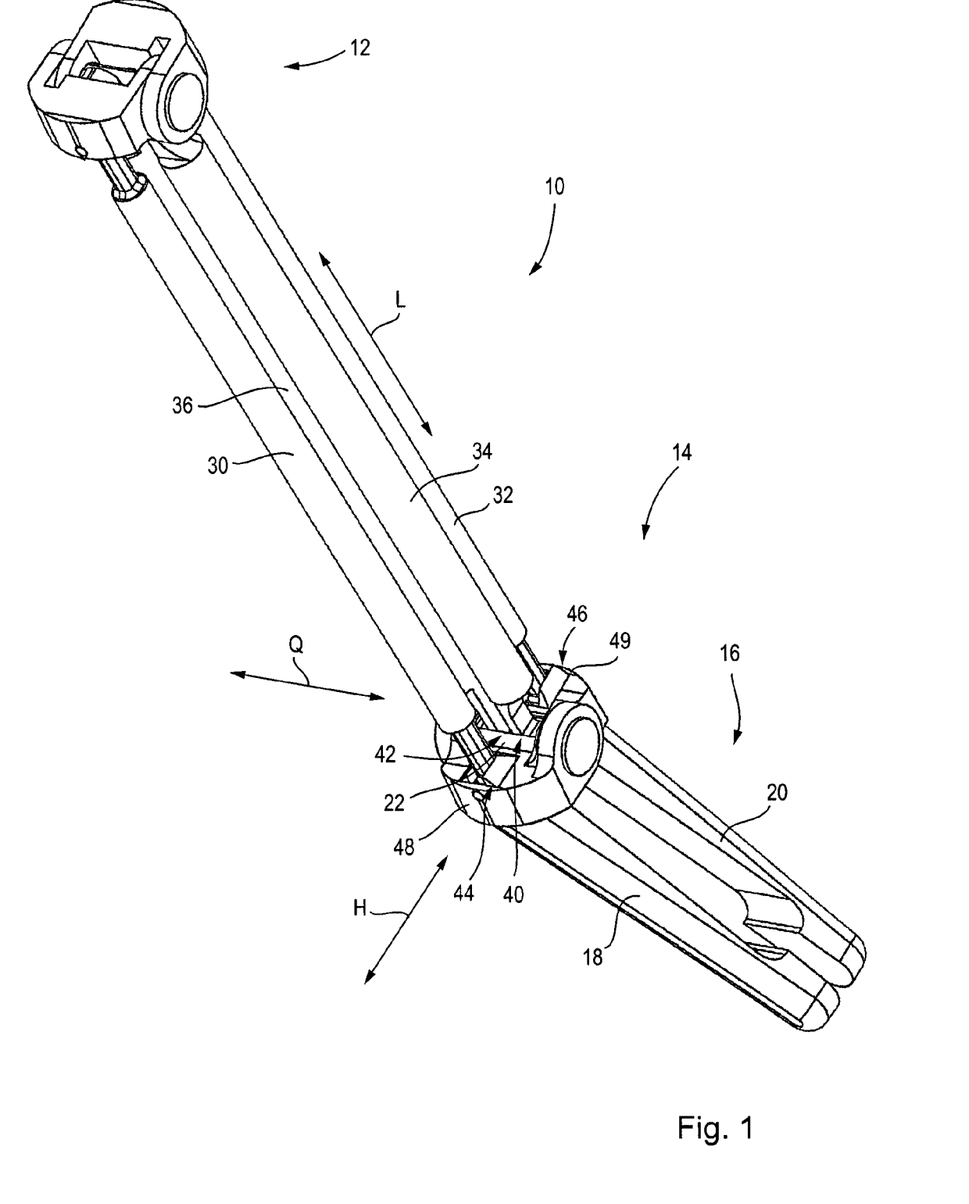
FIG. 1 shows a first exemplary embodiment of an endoscopic instrument in a perspective view.

FIG. 1 shows a first exemplary embodiment of an endoscopic instrument 10 with a proximal end 12 and a distal end 14. For reader guidance, a longitudinal direction L along which the endoscopic instrument 10 extends from the proximal end 12 to the distal end 14, a transverse direction Q which runs perpendicular to the longitudinal direction L, and a vertical direction H are shown, wherein the vertical direction H runs both perpendicular to the longitudinal direction L and also perpendicular to the transverse direction Q.

At the distal end 14, the endoscopic instrument 10 has an end effector 16 which has a first end effector part 18 and a second end effector part 20. Also arranged at the distal end 14 is a connecting element 22 on which the first and second end effector parts 18, 20 are mounted and which extends along the transverse direction Q.

The instrument 10 has a first pushing element 30, a second pushing element 32, a third pushing element 34 and a fourth pushing element 36. The pushing elements 30, 32, 34, 36 extend in each case along the longitudinal direction L and are displaceable relative to one another along the longitudinal direction L.

The first pushing element 30 is articulately arranged at the first end effector part 18. The second pushing element 32 is articulately arranged at the second end effector part 20. The third pushing element 34 is articulately arranged at the connecting element 22, specifically at a third articulation point 40, which is hidden in this case. The fourth pushing element 36 is articulately arranged at the connecting element 22, specifically at a fourth articulation point 42, which is hidden in this case.

The first pushing element 30 is articulately arranged at the first end effector part 18 by a first joint 44. Furthermore, the second pushing element 32 is also articulately arranged at the second end effector part 20 by a second joint 46. Although it is basically possible for at least one of the pushing elements 30, 32 to be rigidly coupled to the respective end effector part 18, 20, the fact that both end effector parts 18, 20 can be moved individually is believed to be helpful.

Also shown are a first holding element 48 and a second holding element 49, the function of which will be explained further below.

Figure 2:
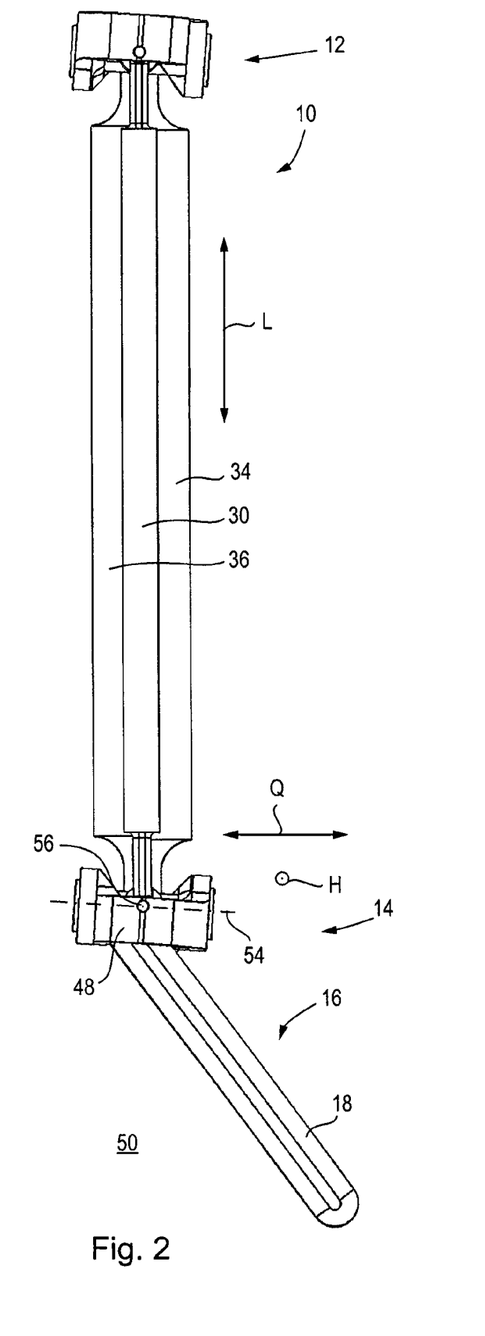
FIG. 2 shows the first exemplary embodiment in a plan view.

FIG. 2 shows the endoscopic instrument 10 as per FIG. 1 in a plan view. Here, the plane of the drawing is the plane spanned by the longitudinal direction L and the transverse direction Q. Said plane is to be understood as the pivot plane 50. The vertical direction H is in this case perpendicular to the pivot plane 50.

Figure 3:
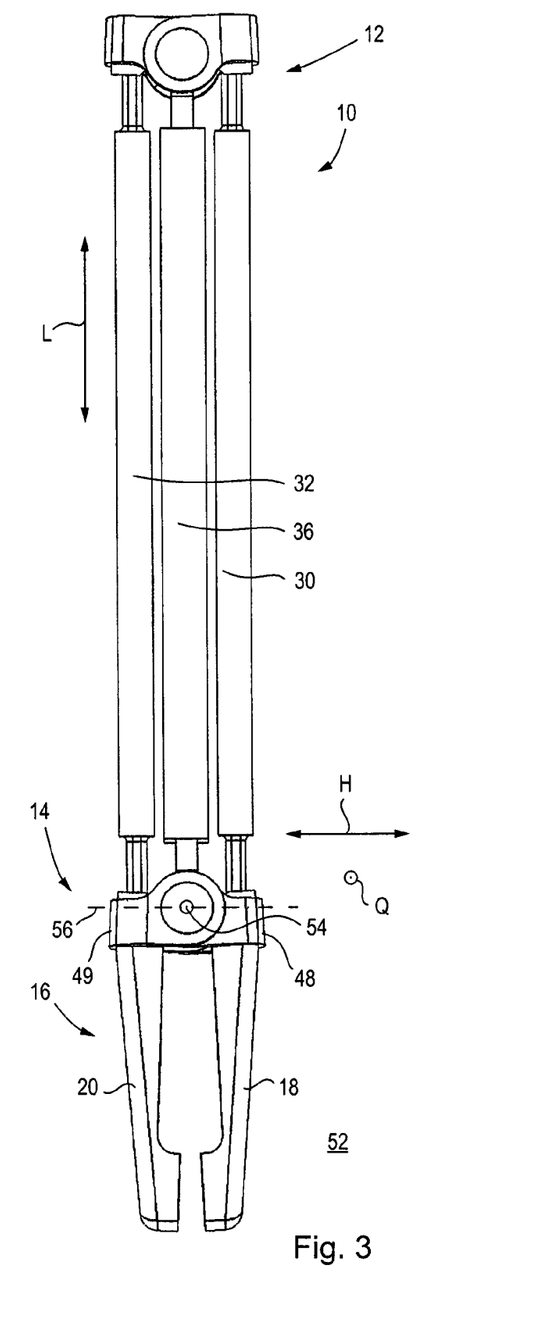
FIG. 3 shows the first exemplary embodiment in a side view.

FIG. 3 shows the endoscopic instrument 10 as per FIG. 1 in a side view. The plane of the drawing is the plane spanned by the longitudinal direction L and the vertical direction H and is denoted by the reference sign 52.

The articulated mounting of the pushing element 30 is configured such that the first end effector part 18 is displaceable relative to the first pushing element 30 parallel to a pivot plane 50 and can be pivoted about a transverse axis 54 of the connecting element 22. As already explained, the pivot plane 50 is an imaginary plane spanned by the longitudinal direction L and the transverse direction Q.

The articulated mounting of the third pushing element 34 is configured such that the third pushing element 34 and the connecting element 22 are pivotable relative to one another about a pivot axis 56. In the plan view as per FIG. 2, the pivot axis 56 is perpendicular to the plane of the drawing. In the side view as per FIG. 3, the pivot axis 56 lies in the plane of the drawing. Here, the transverse axis 54 of the connecting element intersects the pivot axis 56. The articulated mounting of the fourth pushing element 36 is configured such that the fourth pushing element 36 and the connecting element 22 are pivotable relative to one another about the pivot axis 56.

Figure 4:
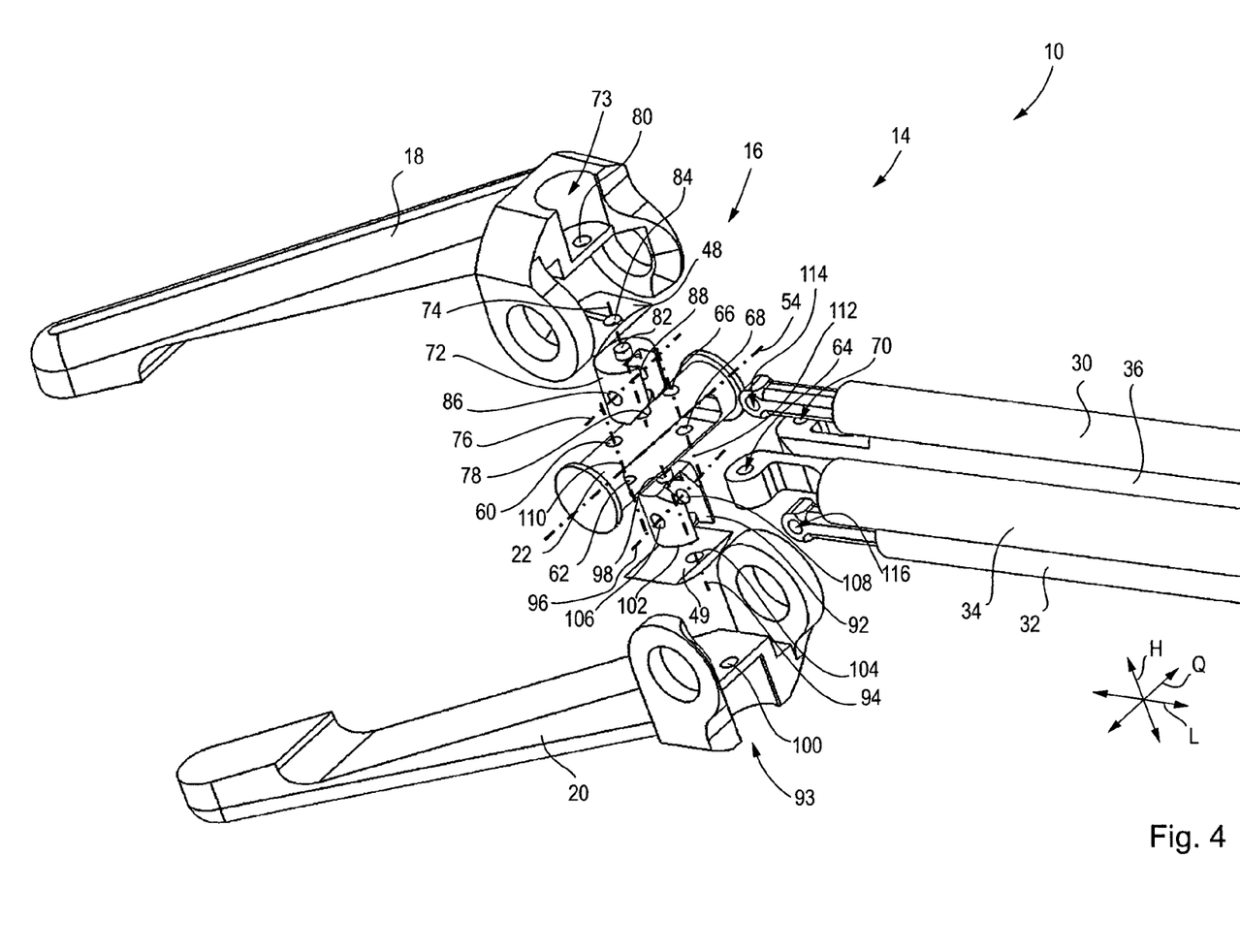
FIG. 4 shows the first exemplary embodiment in an exploded view.

FIG. 4 shows an exploded view of the end effector 16, wherein, for improved clarity, the first end effector part 18 and the second end effector part 20 have been moved outward to a particularly great extent.

The articulated mounting of the third pushing element 34 is configured such that a third pin (not shown) is inserted into a third recess 60 of the connecting element 22 and into a further third recess 62 of the connecting element 22 and, in between, is guided through a third recess 64 on the third pushing element 34. As an alternative to this, the articulated mounting of the third pushing element 34 may be configured such that a projection on the third pushing element 34 engages into a recess 60; 62 of the connecting element 22 or such that a projection on the connecting element engages into the third recess 64 of the third pushing element 34.

The articulated mounting of the fourth pushing element 36 is configured such that a fourth pin (not shown) is inserted into a fourth recess 66 of the connecting element 22 and into a further fourth recess 68 of the connecting element 22 and, in between, is guided through a fourth recess 70 on the fourth pushing element 36. As an alternative to this, the articulated mounting of the fourth pushing element 36 may be configured such that a projection on the fourth pushing element 36 engages into a recess 66; 68 of the connecting element 22 or such that a projection on the connecting element engages into the fourth recess 70 of the fourth pushing element 36.

The first joint 44 has a first joint sleeve 72 which is inserted rotatably into a first recess 73 on the first end effector part 18. The first joint sleeve 72 has a first vertical axis 74 about which the first end effector part 18 can be displaced relative to the first joint sleeve 72. The first joint sleeve 72 has a first transverse axis 76 about which the first pushing element 30 can be displaced relative to the first joint sleeve 72.

The first joint sleeve 72 is inserted by way of a first projection 78 into a first receptacle 80 and is thereby connected in positively locking fashion to the first end effector part 18. The first joint sleeve 72 is furthermore inserted by way of a further first projection 82 into a first receptacle 84 of the first holding element 48. The first joint sleeve 72 furthermore has a first recess 86 and a further first recess 88 through which the first transverse axis 76 runs.

The second joint 46 has a second joint sleeve 92 which is inserted rotatably into a second recess 93 on the second end effector part 20. The second joint sleeve 92 has a second vertical axis 94 about which the second end effector part 20 can be displaced relative to the second joint sleeve 92. The second joint sleeve 92 has a second transverse axis 96 about which the second pushing element 32 can be displaced relative to the second joint sleeve 92.

The second joint sleeve 92 is inserted by way of a second projection 98 into a second receptacle 100 and is thereby connected in positively locking fashion to the second end effector part 20. The second joint sleeve 92 is furthermore inserted by way of a further second projection 102 (hidden) into a second receptacle 104 of the second holding element 49. The second joint sleeve 92 furthermore has a second recess 106 and a further second recess 108 through which the second transverse axis 96 runs.

Also shown in FIG. 4 are the third vertical axis 110 and the fourth vertical axis 112 about which the third pushing element 34 and the fourth pushing element 36, respectively, can be displaced.

The first pushing element 30 is connected in positively locking fashion to the first joint sleeve 72. In this specific embodiment, the positively locking connection is realized by virtue of the fact that a first pin (not shown) is inserted into the first recess 86 and into the further first recess 88 and, in between, is guided through a first recess 114 on the first pushing element 30.

The second pushing element 32 is connected in positively locking fashion to the second joint sleeve 92. In this specific embodiment, the positively locking connection is realized by virtue of the fact that a second pin (not shown) is inserted into the second recess 106 and into the further second recess 108 and, in between, is guided through a second recess 116 on the second pushing element 32.

The first joint sleeve 72 is in this case rotatable only about the first vertical axis 74. The first pushing element 30 is displaceable relative to the first joint sleeve 72 only in an imaginary plane spanned by the longitudinal direction L and the vertical direction H.

The second joint sleeve 74 is in this case rotatable only about the second vertical axis 94. The second pushing element 32 is displaceable relative to the second joint sleeve 92 only in an imaginary plane spanned by the longitudinal direction L and the vertical direction H.

An imaginary elongation of the first vertical axis 74 about which the first end effector part 18 is pivotable relative to the first pushing element 30 runs, with respect to the transverse direction Q, in the center between the articulation points 40, 42 of the third and fourth pushing elements 34, 36 on the connecting element 22.

An imaginary elongation of the second vertical axis 94 about which the second end effector part 20 is pivotable relative to the second pushing element 32 likewise runs, with respect to the transverse direction Q, in the center between the articulation points 40, 42 of the third and fourth pushing elements 34, 36 on the connecting element 22.

All of the pushing elements 30, 32, 34, 36 are arranged parallel to one another. In this case, the pushing elements 30, 32, 34, 36 are designed as pushing rods, and here, are designed to be entirely rectilinear.

In the embodiment shown here, the first end effector part 18 is in the form of a first gripping forceps part and the second end effector part 20 is in the form of a second gripping forceps part. Alternatively, according to some exemplary embodiments, the first end effector part is in the form of a first scissor part, and for the second end effector part 20 to be in the form of a second scissor part. It is understood that it is also possible for other end effector parts to be used.

The structure, and part of the assembly process, of the endoscopic instrument 10 will now be explained step-by-step in the figures that follow.

Figure 5:
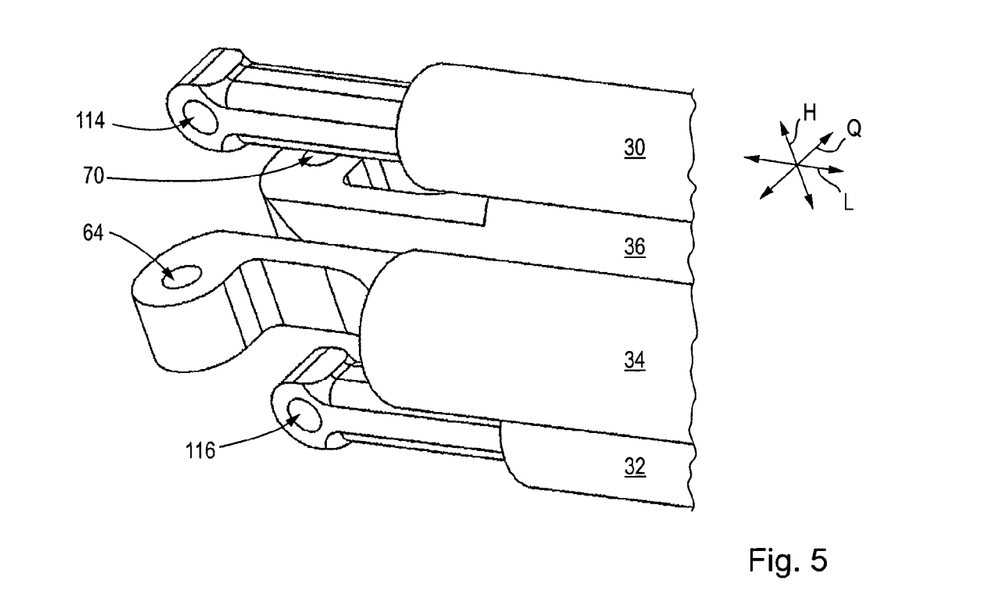
FIG. 5 shows the pushing rods of the first exemplary embodiment.

FIG. 5 shows the four pushing elements 30, 32, 34, 36 with their corresponding recesses 114, 116, 64, 70.

Figure 6:
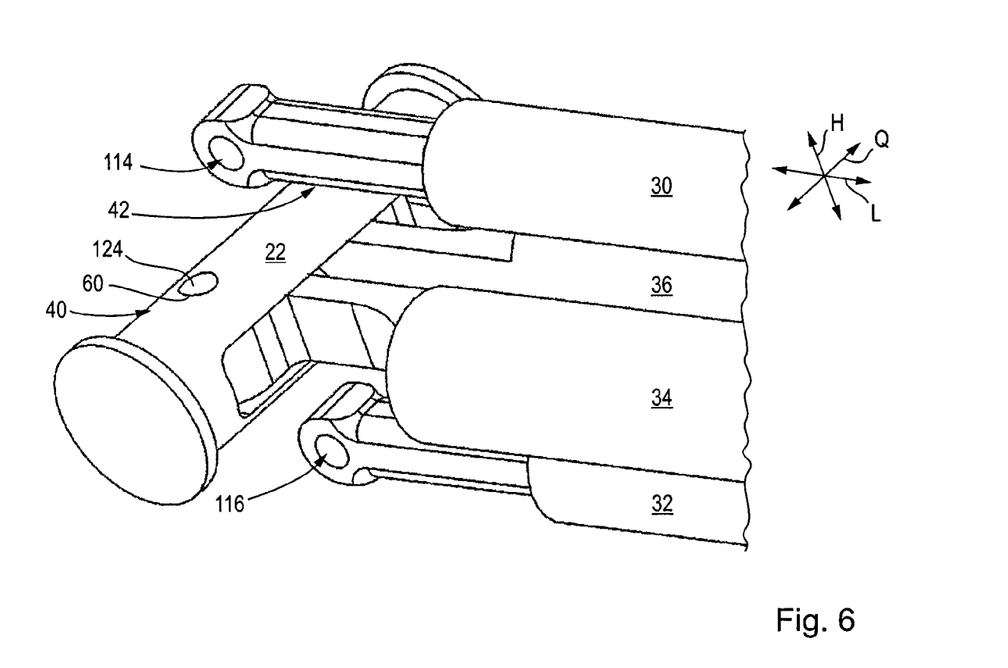
FIG. 6 shows the illustration as per FIG. 5, additionally with the connecting element.

FIG. 6 shows the way in which the third and fourth pushing elements 34, 36 are coupled to the connecting element 22. The third pushing element 34 is coupled to the connecting element 22 by way of a third pin 124 which is inserted into the recess 60 and into the opposite recess 62 (hidden in this case) of the connecting element 22. This produces a third articulation point 40. The fourth pushing element 36 is coupled to the connecting element 22 by a fourth pin (hidden in this case) which is inserted into the recess 64 (hidden in this case) and into the opposite recess 66 (hidden in this case) of the connecting element 22. This produces a fourth articulation point 42 (hidden in this case).

Figure 7:
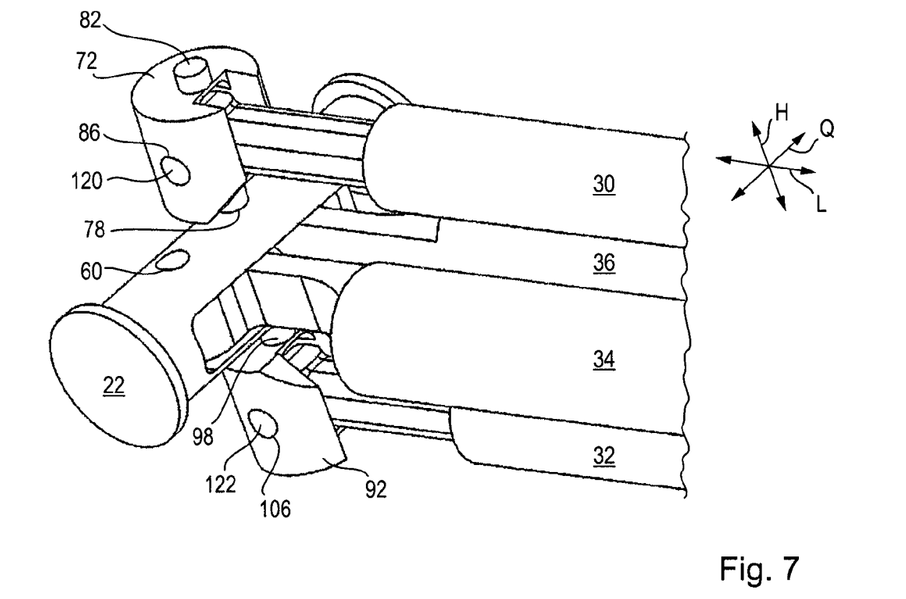
FIG. 7 shows the illustration as per FIG. 6, additionally with joint sleeve.

FIG. 7 additionally shows the way in which the first pushing element 30 is coupled by way of a first pin 120 to the first joint sleeve 72. The figure also shows the way in which the second pushing element 32 is coupled by way of a second pin 122 to the second joint sleeve 92. It can be seen here that the joint sleeves 72, 92 each have a bevel. Since the joint sleeves 72, 92, owing to their coupling to the end effector parts 18, 20, are likewise displaced about the transverse axis 54 of the connecting element 22, an end stop for the opening of the end effector part 16 is thus realized.

Figure 8:
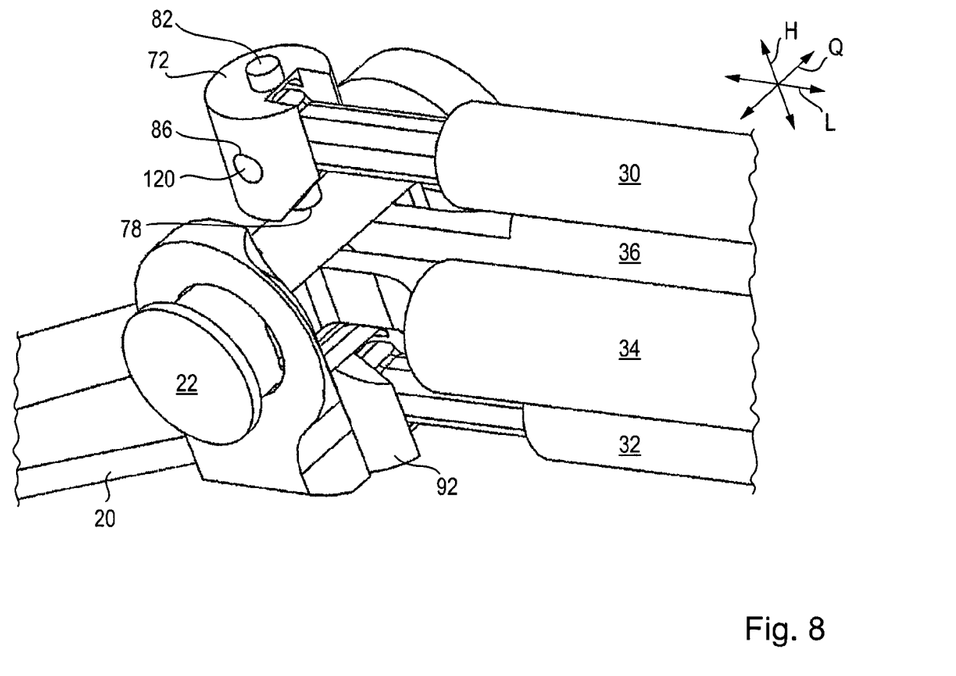
FIG. 8 shows the illustration as per FIG. 7, additionally with the second end effector part.

FIG. 8 additionally shows the second end effector part 20. The second joint sleeve 92 has been inserted into the second recess 93.

Figure 9:
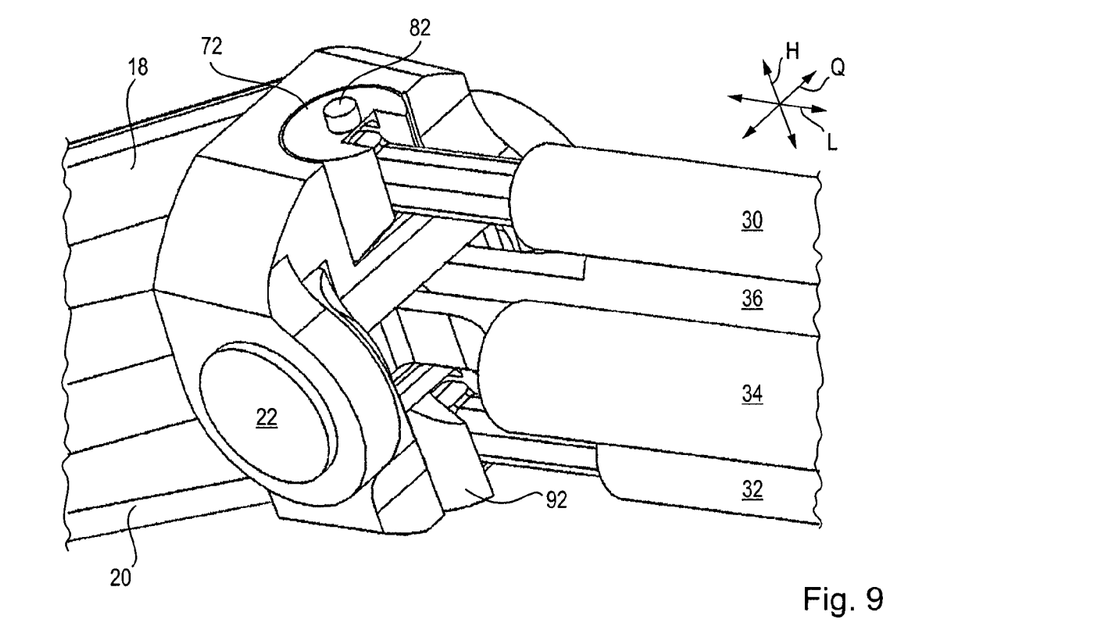
FIG. 9 shows the illustration as per FIG. 8, additionally with the first end effector part.

FIG. 9 additionally shows the first end effector part 18. The first joint sleeve 72 has been inserted into the first recess 73.

Figure 10:
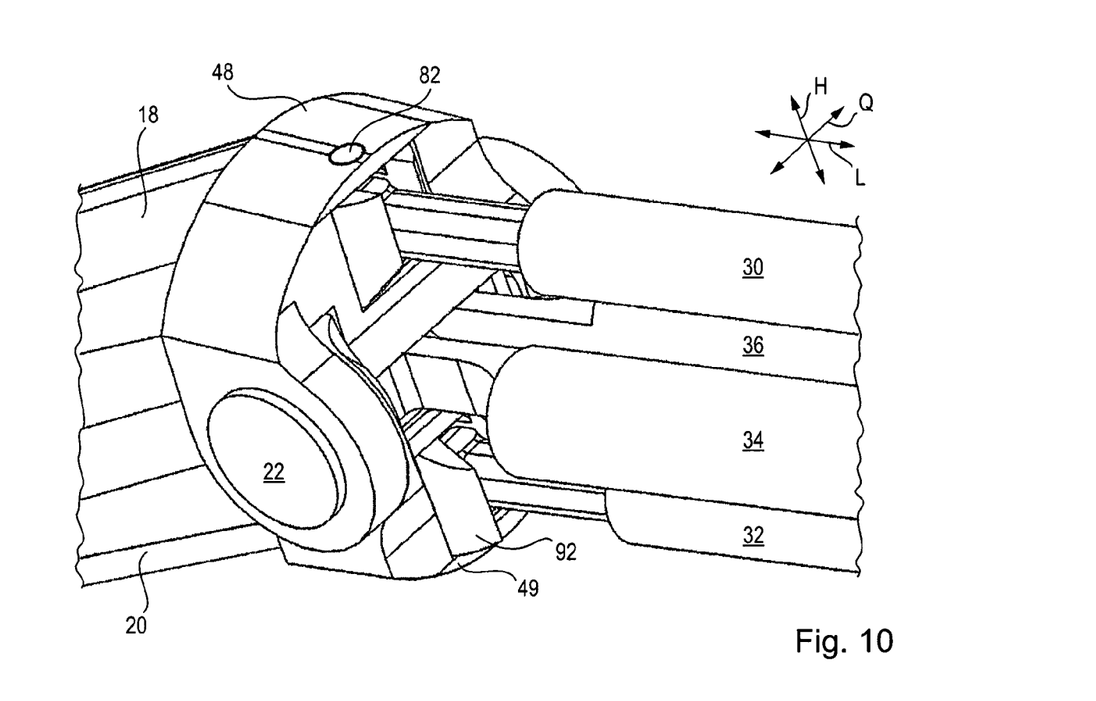
FIG. 10 shows the illustration as per FIG. 9, additionally with covering caps for holding the joint sleeves.

FIG. 10 finally additionally shows the two holding elements 48, 49 which fix the first and second joint sleeves 72, 92.

Figure 11:
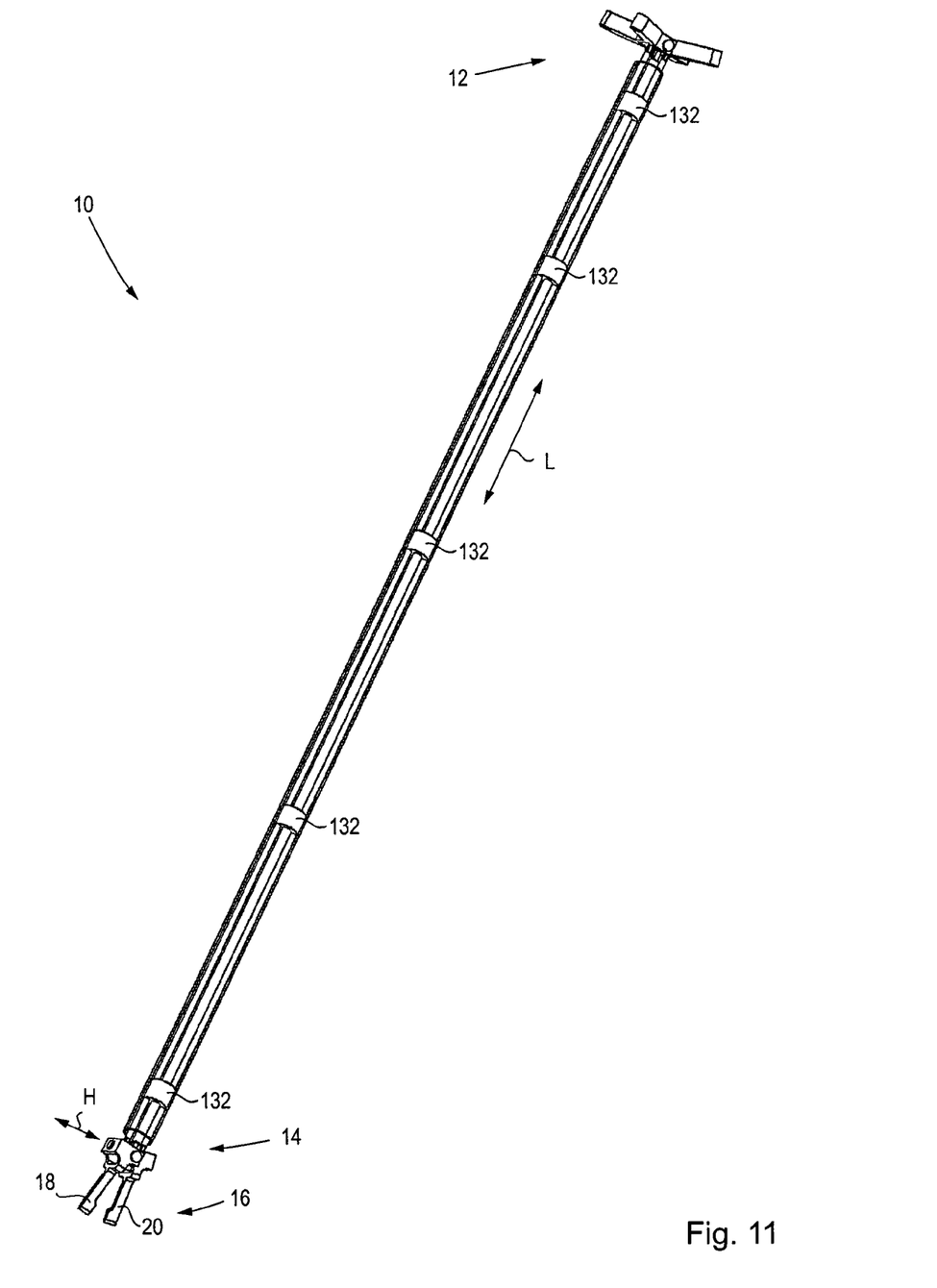
FIG. 11 shows a second exemplary embodiment in a perspective view.

FIG. 11 shows a second exemplary embodiment of an endoscopic instrument 10. Here, those elements which functionally correspond or are functionally similar to the elements introduced previously are likewise denoted by the reference signs introduced previously. Said elements that have been introduced previously will not be described again below.

It can be clearly seen in FIG. 11 that the new concept can also be advantageous for thin endoscopic instruments which have a longitudinal extent several times larger than their cross section.

Figure 12:
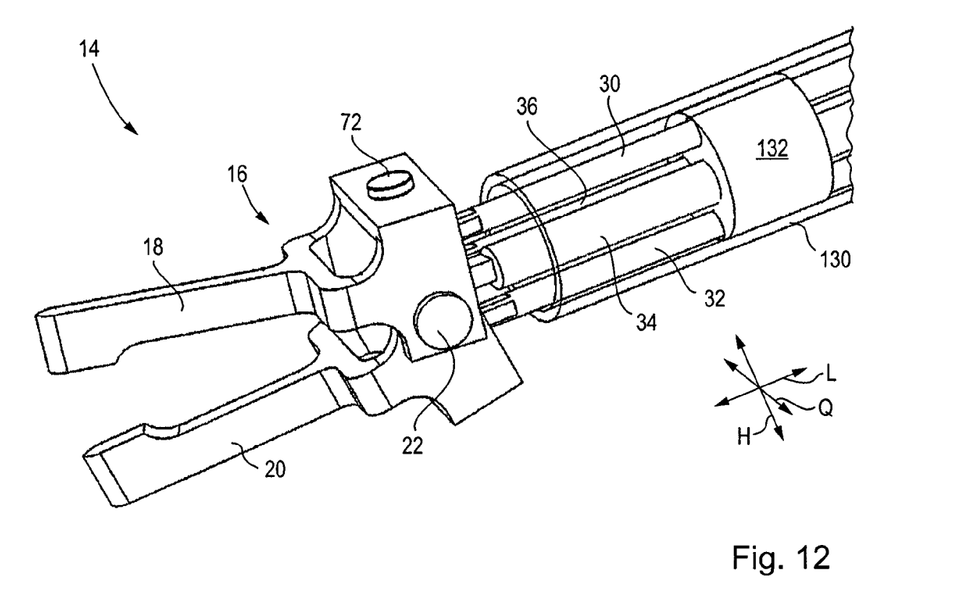
FIG. 12 shows an enlarged view of the distal end of the second exemplary embodiment from a first perspective.

FIG. 12 shows that, in this embodiment, the pushing elements 30, 32, 34, 36 are arranged in a shaft 130 which, for improved understanding, is illustrated in transparent form in this case. For this exemplary embodiment, the guidance of the pushing elements 30, 32, 34, 36 is ensured by guide elements 132 which are arranged in the shaft 130 and through which at least two, according to some exemplary embodiments all, of the pushing elements 30, 32, 34, 36 are guided.

Figure 13:
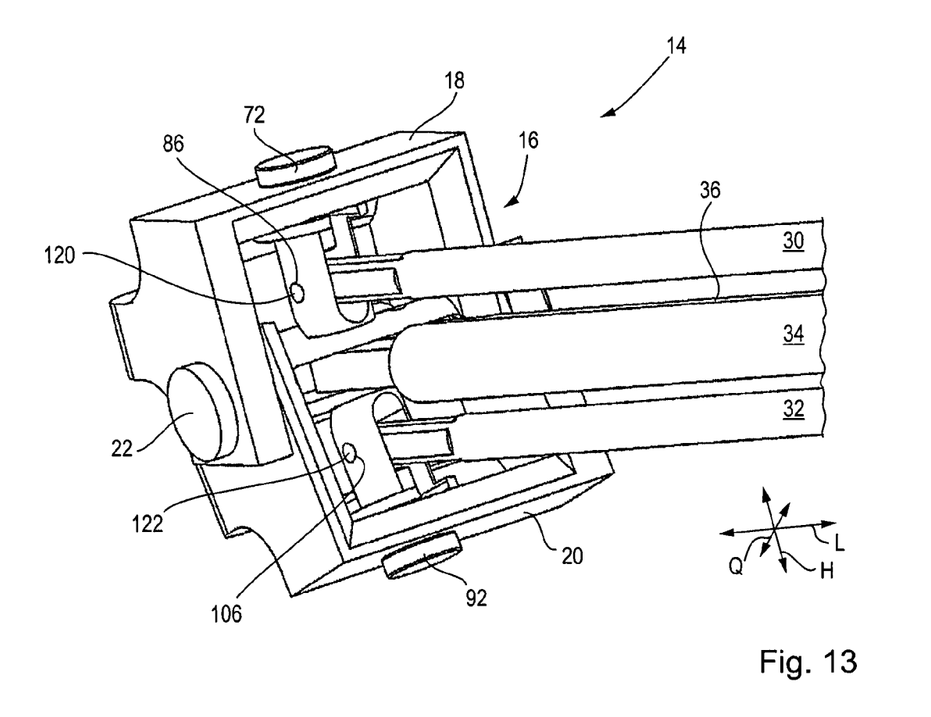
FIG. 13 shows an enlarged view of the distal end of the second exemplary embodiment from a second perspective.

FIG. 13 shows that an alternative configuration of the joint sleeves 72, 92 has also been selected in the second embodiment.

In summary, a new endoscopic instrument 10 has been presented which, with a solution that may be realized with mechanical elements, may offer the surgeon numerous degrees of freedom for the actuation of the end effector and, in so doing, also may permit intuitive operation.

What is claimed is:

1. An endoscopic instrument having
a proximal end,
a distal end,
a longitudinal direction along which the endoscopic instrument extends from the proximal end to the distal end,
an end effector on the distal end, the end effector having a first end effector part and a second end effector part,
a connecting element on the distal end, on which connecting element the first and second end effector parts are mounted and which connecting element extends along a transverse direction,
a first pushing element,
a second pushing element,
a third pushing element, and
a fourth pushing element,
wherein the pushing elements each have a longitudinal axis that extends in the longitudinal direction and are displaceable relative to one another in the longitudinal direction, and wherein the first pushing element is articulately arranged at the first end effector part, the second pushing element is articulately arranged at the second end effector part, the third pushing element is articulately arranged at the connecting element, and the fourth pushing element is articulately arranged at the connecting element.

2. The endoscopic instrument of claim 1, wherein the first pushing element is articulately arranged at the first end effector part by a first joint.

3. The endoscopic instrument of claim 2, wherein the first joint has a first joint sleeve which is inserted rotatably into a recess on the first end effector part.

4. The endoscopic instrument according to claim 3, wherein the first pushing element is connected in positively locking fashion to the first joint sleeve.

5. The endoscopic instrument of claim 3, wherein the first joint sleeve is rotatable only about a first vertical axis that extends in a vertical direction generally perpendicular to both the longitudinal and transverse directions.

6. The endoscopic instrument of claim 3, wherein the first pushing element is displaceable relative to the first joint sleeve only in an imaginary plane which is spanned by the longitudinal direction and a vertical direction that is generally perpendicular to both the longitudinal and transverse directions.

7. The endoscopic instrument of claim 1, wherein the second pushing element is articulately arranged at the second end effector part by a second joint.

8. The endoscopic instrument of claim 1, wherein an articulated mounting of the first pushing element is configured such that the first end effector part is displaceable relative to the first pushing element parallel to a pivot plane and can be pivoted about a transverse axis of the connecting element, wherein the pivot plane is an imaginary plane spanned by the longitudinal direction and the transverse direction.

9. The endoscopic instrument of claim 1, wherein an articulated mounting of the third pushing element is configured such that the third pushing element and the connecting element are pivotable relative to one another about a pivot axis.

10. The endoscopic instrument of claim 1, wherein an articulated mounting of the third pushing element is configured such that a projection on the third pushing element engages into a recess of the connecting element.

11. The endoscopic instrument of claim 1, wherein an articulated mounting of the third pushing element is configured such that a projection on the connecting element engages into a recess of the third pushing element.

12. The endoscopic instrument of claim 1, wherein an articulated mounting of the third pushing element is configured such that a third pin is inserted into two recesses of the connecting element and, between these, is guided through a recess on the third pushing element.

13. The endoscopic instrument of claim 1, wherein a first vertical axis about which the first end effector part is pivotable relative to the first pushing element runs, with respect to the transverse direction, between articulation points of the third and fourth pushing element on the connecting element.

14. The endoscopic instrument of claim 1, wherein a first vertical axis about which the first end effector part is pivotable relative to the first pushing element runs, with respect to the transverse direction, in a center between articulation points of the third and fourth pushing element on the connecting element.

15. The endoscopic instrument of claim 1, wherein a first transverse axis about which the first end effector part is pivotable relative to the first pushing element is at least substantially parallel to the transverse direction.

16. The endoscopic instrument of claim 1, wherein each longitudinal axis of the pushing elements is arranged parallel to the longitudinal axes of the other pushing elements.

17. The endoscopic instrument of claim 1, wherein the pushing elements are designed as pushing rods.

18. The endoscopic instrument of claim 1, wherein he pushing elements are designed entirely rectilinear.

19. The endoscopic instrument of claim 1, wherein the first end effector part is in the form of a first gripping forceps part and the second end effector part is in the form of a second gripping forceps part, or wherein the first end effector part is in the form of a first scissor part and the second end effector part is in the form of a second scissor part.

20. The endoscopic instrument of claim 1, wherein:
the first pushing element articulates the first end effector part about a transverse axis that extends in the transverse direction;
the second pushing element articulates the second end effector part about the transverse axis;
the third pushing element articulates the connecting element about a pivot axis that extends in a vertical direction substantially parallel to the transverse direction and the longitudinal direction; and
the fourth pushing element articulates the connecting element about the pivot axis.

21. The endoscopic instrument of claim 1, wherein the second pushing element articulates the second end effector part about the transverse axis independently of the first end effector part.

* * * * *